United States Patent [19]

Gannon et al.

[11] 4,063,805

[45] Dec. 20, 1977

[54] OPHTHALMIC MEASURING INSTRUMENT

[76] Inventors: Marc Jay Gannon, 24035 Wimbledon, Shaker Heights, Ohio 44122; Daniel Lee Gunter, 1774 Fairview Shores Drive, Orlando, Fla. 32804

[21] Appl. No.: 697,036

[22] Filed: June 17, 1976

[51] Int. Cl.² .......................... A61B 3/10; G01C 5/00
[52] U.S. Cl. .......................................... 351/6; 33/278; 351/5; 351/40; 356/17
[58] Field of Search ............. 351/5, 6, 15, 39, 40; 33/278; 356/17, 32

[56] References Cited
FOREIGN PATENT DOCUMENTS 152,627  2/1938  Austria ............................ 356/17
1,200,026  12/1959  France ............................ 356/17

Primary Examiner—Paul A. Sacher
Attorney, Agent, or Firm—Gary, Juettner & Pyle

[57] ABSTRACT

A measuring instrument particularly adapted to making accurate measurements of portions of the eye and contact lenses is characterized by a split mirror system in which one mirror is fixed and a second mirror rotates upon movement of handle-pointer associated with a scale. The object to be measured is magnified, and the magnified image is split by the mirror system until opposite edges of the split image coincide, whereby a correlated linear measurement is indicated on the scale. The instrument includes a light to illuminate the work area and an attachment for measuring the diameter of contact lenses.

16 Claims, 9 Drawing Figures

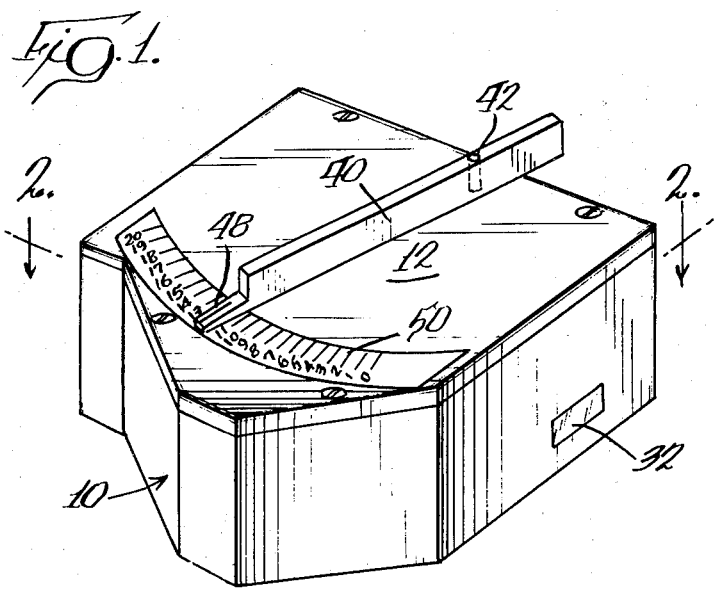
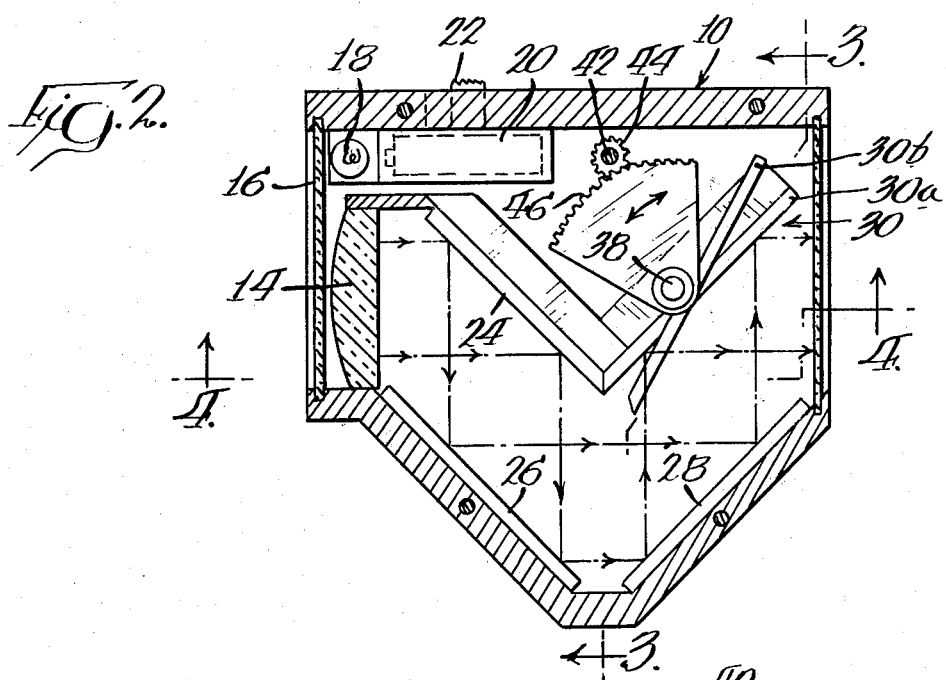
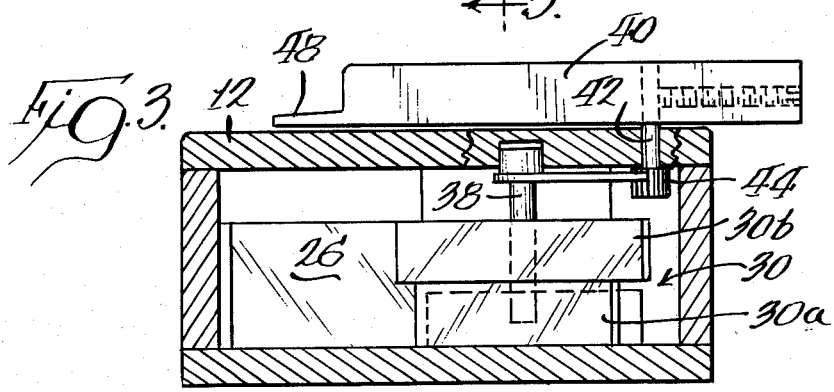

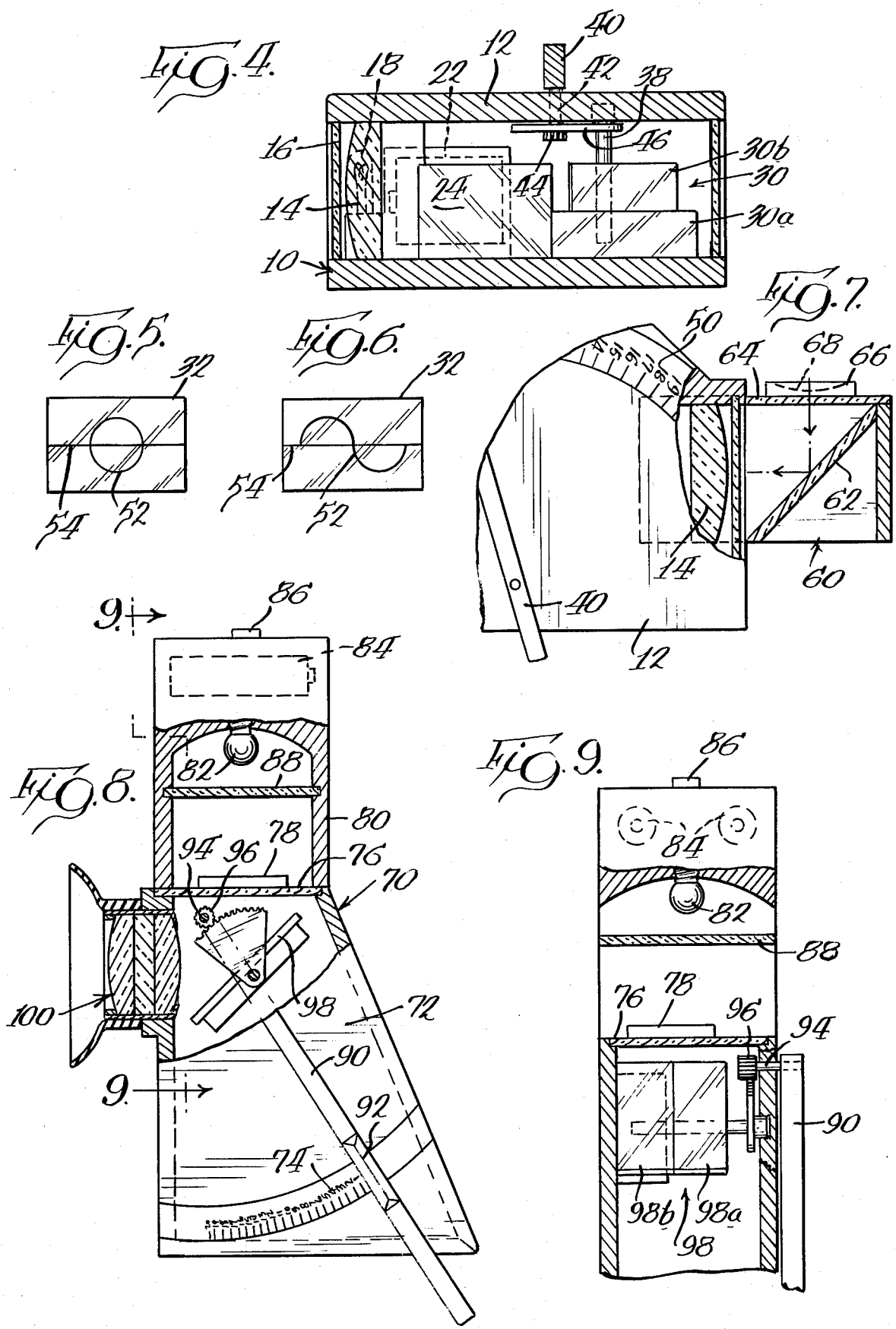

OPHTHALMIC MEASURING INSTRUMENT

BACKGROUND OF THE INVENTION

The proper fitting of contact lenses involves various ophthalmic measurements, such as iris diameter, pupil diameter, height of the palpebral fissure, as well as parameters of the contact lens. Unfortunately, present day instruments and methods used for making such measurements are generally inefficient, cumbersome, or unduly expensive.

Measurements of the pupil, iris and fissure are currently made with the use of a hand held graduated rule or a reticle used with a simple magnifier or a more sophistocated slit lamp. The use of the rule is subject to the accuracy of the markings on the rule, elimination of eye movement during measuring, elimination of parallax errors and unwanted shadows. Even the most sophistocated systems, however, have an accuracy of about ±0.3 mm, whereas proper fitting of some types of contact lenses require accuracy within ±0.1mm.

None of the above instruments are used to measure the parameters of contact lenses, such as overall diameter, optical zone, and peripheral curve. Instead, a separate instrument is employed and usually comprises a 7×magnifier having a reticle with scale markings. Proper use of the instrument requires exact positioning of the lens relative to the scale, which is often a cumbersome procedure.

In summary, there is presently no instrument capable of making highly accurate and reliable measurements of the eye, and no single instrument capable of making measurements of both the eye and the contact lens.

SUMMARY OF THE INVENTION

The present invention provides a simple and inexpensive instrument and method for accurately making all measurements of the eye required for the fitting of contact lenses, as well as measurements of the individual lens. The device is capable of measurements of a tolerance less than 0.1mm for any object or image having reasonably distinct boundaries or edges and is particularly suitable for ophthalmic measurements.

The device is characterized by a housing having a magnifier in one portion and a viewing aperture in another portion. The object to be measured is magnified and reflected toward the viewer by an internal split mirror system. The mirrors are mounted in a coplanar relationship, and one mirror may be rotated out of the plane of the other. The degree of rotation is controlled manually with an external handle that is associated with a graduated scale on the body of the housing.

With mirrors in a coplanar relationship, the magnified image viewed through the viewer appears whole. Upon rotation, the image is split into two parts, and rotation is continued until opposite edges of the parts coincide. The degree of rotation is directly correlated to the linear dimension being measured, and such dimension is indicated on the graduated scale.

From the foregoing, it may be seen that a measurement operation requires merely aligning the object through the viewer and rotation of the handle to make a measurement, which is simple, reliabile, and less time consuming than existing methods.

The device may include right angle reflecting attachments to allow for more convenient viewing of a particular article, as well as internal light sources for illuminating the work area.

THE DRAWINGS

FIG. 1 is a perspective view of the measuring instrument of the present invention.

FIG. 2 is a cross-sectional view taken along line 2—2 of FIG. 1.

FIG. 3 is a cross-sectional view taken along line 3—3 of FIG. 2.

FIG. 4 is a cross-sectional view taken along line 4—4 of FIG. 2.

FIGS. 5 and 6 are views through the viewing aperture of the instrument, illustrating a representation of an object during the measurement procedure.

FIG. 7 is a fragmentary plan view of the instrument shown in FIG. 1, further illustrating an attachment thereto.

FIG. 8 is an elevational view, partly in a cross section, of another embodiment of the instrument of the present invention.

FIG. 9 is a sectional view taken along line 9—9 of FIG. 8.

DECRIPTION OF THE PREFERRED EMBODIMENTS

As shown in FIGS. 1-4, the instrument of the present invention is contained and supported within a suitable housing 10, which may have a removable top cover 12 to allow access to the interior.

Mounted at one end of the housing is a magnifying lens 14, preferably a 5x aspheric lens system, for magnifying the object to be viewed. The lens is preferably surrounded by an opaque side wall 16 to allow transmission of light from the interior of the housing toward the object. A suitable internal light source may be provided, such as the bulb 18 connected in a known fashion to a battery 20 and operated by a switch 22 accessible externally of the housing 10.

Mounted within the housing and behind the lens 14 is a series of equi-sized fixed mirrors 24, 26 and 28 (FIG. 2), the purpose of which are to reflect the magnified image from the lens onto a split mirror system, generally indicated at 30, and thence out of a viewing aperture 32 located behind and in direct alignment with the lens. The first fixed mirror is located directly behind the lens 14 and at a 45° angle to the axis thereof, whereby the image is reflected from the mirror at a 90° angle. The second mirror 26 is mounted out of the path of the lens 14 in rearward parallel relationship with the first mirror 24, whereby the image from the first mirror is reflected by the second mirror 90° to the rear. The third fixed mirror 28 is located rearwardly of the second mirror and at an angle of 90° thereto, and the split mirror system 30 is arranged rearwardly with the first mirror 24 in parallel with the third mirror. The three fixed mirrors 24, 26 and 28 thus serve to reflect the image back to the split mirror system 30, which is disposed at 45° to the viewing aperture 32.

It will be appreciated that the fixed mirrors 24, 26 and 28 are utilized for convenience and serve to bend light around two corners of a square. This feature allows the viewing aperture 32 to be located in direct rearward alignment with the lens 14, allowing the user to face the subject being examined and giving the sensation that the image is moving in a straight path from the lens to the viewing aperture. Other mirror systems could be employed to allow viewing from any desired position relative to the lens.

The split mirror system 30 comprises a pair of mirror segments 30a and 30b which are contiguous and together define a mirror of the same size as the fixed mirrors. The lower segment 30a is affixed in the housing in parallel relationship with the third mirror 28. The upper mirror segment 30b is rotatable about a central axis from a position coplanar with lower segment 30a to positions at an angle relative to the lower segment. For this purpose, the rear side of rotatable segment 30b is affixed to a shaft 38 on the central axis of the mirror, said shaft being journalled at or near its free ends in the housing 10.

Means are provided for rotating the shaft 38 and the mirror segment 30b while at the same time indicating the degree of rotation. In accordance with the preferred embodiment, an external handle 40 is rotatably connected to the housing and connected by a motion reducing system to the shaft 38, whereby a relatively large degree of rotation of the handle is required to effect a small degree of rotation of the shaft.

As shown, the handle 40 is mounted near one end on a shaft 42 journalled through a wall of the housing 10 and terminating in a pinion 44. The pinion 44 is engaged with a relatively large diameter circular gear segment 46, said segment being affixed on its axis to the shaft 38. It may be seen that a relatively large rotation of the handle 40 and pinion 44 is required to effect a small degree of rotation of the shaft 38 and mirror segment 30b. As will be explained hereinafter in more detail, this feature in effect magnifies or multiplies the degree of movement of the mirror segment 30b, which is directly related to the measurement being sought, thus greatly increasing the accuracy of the instrument.

The other end of the handle 40 preferably terminates in a pointer 48 or other reference indicator, and a curved reference scale 50 (FIG. 1) is located thereunder. The scale 50 may be applied to the exterior surface of the housing and may be divided into any desired units of measure. The handle 40 is arranged such that the pointer 48 slides or moves across the scale 50, with the radius of the circular arc of the scale corresponding substantially with the radius from the pivot of the handle to the pointer. The curved scale associated with the pointer allows the rotational angle of the mirror segment 30b relative to the mirror segment 30a to be read as linear units of measure.

The operation of the device shown in FIGS. 1–4 will now be described with reference to FIGS. 5 and 6. Assuming that the diameter of a pupil is to be measured, the instrument is positioned with the lens 14 facing the eye of the subject, and the operator views through the viewing aperture 32, corresponding to the views shown in FIGS. 5 and 6. The pointer 48 is placed in the zero position, under which condition the mirror segments 30a and 30b are coplanar. In such case, the outline of the pupil, indicated at 52, will appear as a circle that is bisected by the juncture line 54 between the lens segments.

In order to make the measurement, the handle 40 is rotated, causing the mirror segment 30b to rotate relative to the segment 30a. The handle is rotated until half of the image is split and moved its entire width, diameter, or length, as shown in FIG. 6, whereby opposite edges of the image coincide. The degree of movement required to move the image of the half segment along a distance of the length thereof is directly calibrated as a unit linear measurement on the scale 50, and corresponds to the length or diameter of the object being moved.

From the above, it may be seen that the amplified degree of movement of the handle 40 and pointer 48 is correlated directly to the degree of rotation of the mirror segment 30b relative to the segment 30a, which is in turn correlated to the width, length or diameter of the object being observed and measured. Although the operation of the instrument has been described as having a null or reference point as zero, it is obvious that the null point, i.e., corresponding to the setting in which the mirror segments 30a and 30b are coplanar, could represent any value on the scale 50, since only the degree of rotation is measured with regard to a reference point.

A contact lens measuring attachment for the instrument illustrated in FIGS. 1–4 is shown in FIG. 7 and is generally indicated at 60. The instrument described hereinbefore in connection with FIGS. 1–4 is intended to view vertical objects along a horizontal line with the instrument in a horizontal position. The attachment 60 allows an object to be supported horizontally and viewed and measured with the instrument in a horizontal position.

The attachment 60 comprises a housing that is attached or capped by means (not shown) over the lens 14. An upwardly facing reflective mirror 62 is mounted in the housing in front of the lens 14 at a 45° angle thereto. The housing 60 includes a top wall 64 having a holder 66 with a dished-out well 68 therein for receiving and supporting a contact lens therein. The wall 64 and holder 66 are constructed of transparent material to allow the image of the horizontally supported contact lens to be reflected by the mirror 62 and into the lens 14, with the measurement being made by the same method hereinbefore described.

Another embodiment of the invention, particularly suitable for measuring the parameters of contact lenses, is shown in FIGS. 8 and 9. The device therein shown comprises a housing 70 having a side wall 72 with a curved scale 74 thereon and an upper transparent wall 76 bearing a lens holder 78. Mounted on the top wall is a secondary housing 80 containing a light source including bulb 82, battery 84 and external switch 86 mounted in the top of the secondary housing. An screen 88 is mounted in the housing between the bulb 82 and the holder 78 to diffuse the light from the bulb.

In the present embodiment, a similar handle 90 having a reference indicator 92 is utilized, one end of which is connected to a shaft 94 and gear system 96 similar to that hereinbefore described. The shaft 94 is secured to one segment 98a of a split mirror system, the other segment 98b of which is fixed at a 45° angle relative to a magnifying eyepiece 100 located on the side of the housing. The mirror 98b is also arranged at 45° to the holder 78 and to the lens contained therein, whereby the image of the lens is reflected by the mirrors 98a and 98b into the eyepiece 100.

The operation of the device of the present embodiment is similar to that previously described except that the series of fixed mirrors is eliminated and the object is measured at right angles to the viewer. In measuring a contact lens, for example, the lens is simply placed in the holder 78 and the distance between the whole image and the split image is measured on the scale 74 as a linear measurement.

It will be understood that various modifications, changes in design and other alterations to the embodiments described herein may be made without departing from the scope and spirit of the invention defined in the claims appended hereto. For example, although the instruments described herein are especially suitable for measurements relating to the eye and to contact lenses, it will be appreciated that the instrument could be easily adapted and used for making linear measurements of any object or image.

We claim:

1. An instrument for measuring a dimension between an object being viewed, comprising focusing means for viewing said object at a given distance, a pair of mirrors arranged in a common plane on an angle facing said object, one of said mirrors being fixed relative to said object, the other of said mirrors being rotatable relative to said one mirror, the image of said object being divided into a split image upon rotation of said other mirror out of planar relationship with said one mirror, means for rotating said other mirror, and means for correlating the relative degree of rotation of said other mirror to the dimension being measured.

2. The instrument according to claim 1 further comprising means for magnifying the image of said object on said mirrors.

3. The instrument of claim 1 wherein the means for measuring the degree of rotation of said other mirror comprises a scale, and means rotatable with said other mirror in correlation with said scale.

4. The instrument of claim 3 wherein the means rotatable with said other mirror comprises motion multiplying means for multiplying the degree of rotational movement of said other mirror.

5. A measuring instrument comprising a housing, magnifying lens means for magnifying objects externally of said housing, a pair of contiguous coplanar mirrors in said housing arranged to reflect the magnified image of said lens, one of said mirrors being fixed with respect to said lens and the other of said mirrors being rotatable out of coplanar relation with said one mirror, means for viewing the object reflected by said mirrors, manually operable means for rotating said other mirror, and means for measuring the degree of movement of said manually operable means.

6. The instrument of claim 5, wherein the means for viewing said object is located behind the lens means, and wherein said instrument further comprises fixed reflective means in said housing for reflecting the image of said lens means onto said mirrors.

7. The instrument of claim 5 wherein said means for measuring the movement of said manually operable means comprises a linear scale correlated with said manually operable means.

8. The instrument of claim 5 wherein said manually operable means comprises gear means for multiplying the degree of movement of said manually operable means required to rotate said other means.

9. The instrument of claim 7 wherein said manually operable means comprises a handle movable in register with said scale, a first circular gear connected to said handle for rotation thereby, a second circular gear meshed with said first gear and having a larger diameter than said first gear, and a shaft connected to and rotated by said second gear, said shaft being secured to said other mirror for rotation thereof.

10. The measuring instrument of claim 5 further comprising illuminating means associated with said housing for illuminating said object.

11. The measuring instrument of claim 5 further comprising means for reflecting the image of said object at right angles into said lens means.

12. The measuring instrument of claim 11 wherein said means for reflecting the image of said object further comprises means for illuminating said object.

13. A method of making a measurement of an object between points on opposite edges of said object, comprising the steps for providing a whole reflected image of said object upon a pair of coplanar contiguous mirrors, such that the juncture between the mirrors is in alignment with said points, rotating one of said mirrors while holding the other mirror fixed until the image is split and said opposite edges coincide, and measuring the degree of rotation of said one mirror in correlation with units of measure.

14. The method according to claim 13 comprising the further step of magnifying the object reflected by the mirrors.

15. The method according to claim 13 wherein the step of measuring the rotation of said one mirror comprises correlating said degree of rotation to linear units of measure.

16. The method according to claim 13 wherein the step of measuring the degree of rotation of said one mirror comprises the further step of amplifying said rotation in correlation with said units of measure.

* * * * *